United States Patent [19]
Burgess et al.

[11] Patent Number: 5,820,852
[45] Date of Patent: Oct. 13, 1998

[54] ORAL COMPOSITIONS CONTAINING FLUORIDE, PYROPHOSPHATE, AND PEROXIDE

[75] Inventors: Steven Carl Burgess, Sharonville; Connie Lynn Sheets, Cincinnati, both of Ohio

[73] Assignee: The Proctor & Gamble Company, Cincinnati, Ohio

[21] Appl. No.: 756,740

[22] Filed: Nov. 26, 1996

[51] Int. Cl.⁶ .............................. A61K 7/16; A61K 7/18; A61K 7/20

[52] U.S. Cl. ................. 424/52; 424/49; 424/53; 424/57

[58] Field of Search ........................... 424/49–58

[56] References Cited

U.S. PATENT DOCUMENTS

| | | | |
|---|---|---|---|
| 4,925,655 | 5/1990 | Smigel et al. | 424/52 |
| 5,256,402 | 10/1993 | Prencipe et al. | |
| 5,292,502 | 3/1994 | Burke et al. | 424/54 |
| 5,296,215 | 3/1994 | Burke et al. | 424/49 |
| 5,372,803 | 12/1994 | Williams et al. | 424/53 |
| 5,403,578 | 4/1995 | Gordon . | |
| 5,424,059 | 6/1995 | Prencipe et al. | 424/52 |
| 5,456,902 | 10/1995 | Williams et al. | 424/49 |
| 5,456,903 | 10/1995 | Huetter et al. | |
| 5,496,541 | 3/1996 | Cutler | 424/50 |
| 5,565,190 | 10/1996 | Santalucia et al., II | 424/53 |
| 5,571,501 | 11/1996 | Toy . | |
| 5,597,554 | 1/1997 | Wagner . | |
| 5,599,527 | 2/1997 | Hsu et al., IV . | |
| 5,624,906 | 4/1997 | Vermeer . | |

FOREIGN PATENT DOCUMENTS

| | | | |
|---|---|---|---|
| 2162812 | 5/1996 | Canada | A61K 7/20 |
| 2162821 | 5/1996 | Canada | A61K 7/20 |
| 2162885 | 5/1996 | Canada | A61K 7/20 |
| 0 712 624 A2 | 5/1996 | European Pat. Off. | A61K 7/16 |
| 2079325 | 1/1996 | Spain | A61K 7/28 |

OTHER PUBLICATIONS

U.S. application No. 08/334,635, Huetter, filed Nov. 4, 1994.
U.S. application No. 08/365,975, Huetter, filed Dec. 28 1994.
U.S. application No. 08/756450, Burgess, et al. Nov. 26, 1996.
U.S. application No. 08/756,671, Sanker, et al., Nov. 26, 1996.
U.S. application No. 08/756,995, Burgess et al., Nov. 26, 1996.
U.S. application No. 08/756,015, Burgess, et al., Nov. 26, 1996.

*Primary Examiner*—Shep K. Rose
*Attorney, Agent, or Firm*—Angela Marie Stone; Mary Catherine Hentz; Douglas C. Mohl

[57] ABSTRACT

The present invention relates to an oral compositions comprising a soluble fluoride ion source, tetrasodium pyrophosphate, calcium peroxide, and one or more aqueous carriers, wherein the oral composition has a neat pH of from about 9.0 to about 10.5 and a total water content of from about 9.1% to about 20%. The invention may also include an alkali metal bicarbonate salt and xylitol.

20 Claims, No Drawings

ORAL COMPOSITIONS CONTAINING FLUORIDE, PYROPHOSPHATE, AND PEROXIDE

BACKGROUND OF THE INVENTION

The present invention relates to stable oral compositions containing fluoride, pyrophosphate, and calcium peroxide, wherein the total water content and pH are controlled.

Oral compositions utilizing a peroxide component are known. The most widely used peroxide has been hydrogen peroxide. Compositions containing peroxide generally deliver benefits in the antiplaque and antigingivitis areas. Other cosmetic benefits, such as tooth whitening, may also be provided. Oral compositions formulated with peroxide, a highly reactive ingredient, generally exhibit poor stability and many products do not have consumer preferred aesthetics.

While peroxide executions have been developed, they present a processing and stability challenge. Producing stable peroxide compositions also containing tartar control ingredients and fluoride in the same phase is even more difficult. It is difficult to stabilize the peroxide in the presence of fluoride and tartar control ingredients, without producing a product which has negative aesthetics and tartar control efficacy concerns.

References disclosing peroxide containing compositions include U.S. Pat. No. 5,403,578, to Gordon, issued Apr. 4, 1995, which discloses an oral composition containing peroxide, a tartar control ingredient, and fluoride. To stabilize the peroxide, the peroxide is microencapsulated to avoid the peroxide reacting with the other ingredients. U.S. Pat. Nos. 5,456,902, to Williams, et al., issued Oct. 10, 1995, and 5,372,803, to Williams, et al., issued Dec. 13, 1994, disclose a composition utilizing a dual-compartment dispenser which separates the peroxide phase from the tartar control ingredients. WO 95/09603, published Apr. 13, 1995, also discloses a dual-compartment container which separates a calcium peroxide phase from the other dentifrice phase.

Canadian published applications 2,162,821, 2,162,885, and 2,162,812, all published May 15, 1996, disclose the use of calcium peroxide in a dentifrice. The amount of the water is controlled in these applications to aid in the stability.

Although peroxide products containing tartar control ingredients and fluoride are known, there is a continuing need to develop improved products. The present inventors have discovered that a stable oral composition can be formulated to include a soluble fluoride ion source, pyrophosphate, and calcium peroxide by controlling the total water content and the pH. It has also been discovered that these oral compositions may also contain an alkali metal bicarbonate salt and xylitol while still maintaining good stability.

It is therefore an object of the present invention to provide a stable tartar control composition that contains a soluble fluoride ion source and calcium peroxide. It is also an object of the present invention to provide a tartar control composition that contains a soluble fluoride ion source, calcium peroxide, an alkali metal bicarbonate salt, and xylitol. A further object of the present invention is to provide compositions which deliver a variety of benefits to the mouth, such as those described above, and compositions having improved aesthetics.

These and other objects of the present invention will become readily apparent from the detailed description which follows.

All percentages and ratios used herein are by weight of the total composition, and all measurements are made at 25° C., unless otherwise specified.

SUMMARY OF THE INVENTION

The present invention relates to an oral composition comprising a soluble fluoride ion source capable of providing from about 50 ppm to about 3500 ppm of free fluoride ions, an amount of at least about 1.5% tetrasodium pyrophosphate, from about 0.01% to about 5% of calcium peroxide, and from about 80% to about 98% of one or more aqueous carriers, wherein the oral composition has a neat pH of from about 9.0 to about 10.5 and a total water content of from about 9.1% to about 20%. The invention may also include from about 0.5% to about 40% of an alkali metal bicarbonate salt and from about 0.01% to about 25% of xylitol.

DETAILED DESCRIPTION OF THE INVENTION

The present invention relates to oral compositions comprising fluoride, tetrasodium pyrophosphate, and calcium peroxide. These compositions can also include an alkali metal bicarbonate salt and xylitol.

The oral compositions of the present invention may be in the form of a toothpaste. The term "toothpaste", as used herein, means paste, gel, or liquid formulations unless otherwise specified. The toothpaste may be in any desired form, such as deep striped, surface striped, mulitlayered, having the gel surrounding the paste, or any combination thereof. The toothpaste may also be a multilayer composition which is extruded from the tube in combination paste/gel stripes. One of the layers must comprise all of the essential components, while the other layers may contain less than all of the essential components or may be any dentifrice formulation.

The term "oral composition" as used herein means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

The term "aqueous carrier" as used herein means any safe and effective materials for use in the compositions of the present invention. Such materials include thickening materials, humectants, water, buffering agents, abrasive polishing materials, surfactants, titanium dioxide, flavor system, sweetening agents, coloring agents, and mixtures thereof.

The present compositions comprise essential components, as well as optional components. The essential and optional components of the compositions of the present invention are described in the following paragraphs.

Fluoride Ion Source

The present invention incorporates a soluble fluoride source capable of providing free fluoride ions. Preferred soluble fluoride ion sources include sodium fluoride, stannous fluoride, indium fluoride, and sodium monofluorophosphate. Sodium fluoride is the most preferred soluble fluoride ion source. Norris et al., U.S. Pat. No. 2,946,725, issued Jul. 26, 1960, and Widder et al., U.S. Pat. No. 3,678,154 issued Jul. 18, 1972, disclose such fluoride ion sources as well as others. Both patents are incorporated herein by reference in their entirety.

The present compositions contain a soluble fluoride source capable of providing from about 50 ppm to about 3500 ppm, and preferably from about 500 ppm to about 3000 ppm of free fluoride ions.

Pyrophosphate Source

The present invention also includes a pyrophosphate source. The pyrophosphate source comprises predominately undissolved pyrophosphate. Undissolved pyrophosphate compositions are defined as compositions containing no more than about 20% of the total pyrophosphate salt dissolved in the composition, preferably less than about 10% of the total pyrophosphate dissolved in the composition. Tetrasodium pyrophosphate salt is the preferred pyrophosphate salt in these compositions. It is also preferred that tetrasodium pyrophosphate be the only pyrophosphate or tartar control agent used.

Tetrasodium pyrophosphate may be the anhydrous salt form or the decahydrate form, or any other species stable in solid form in the dentifrice compositions. The anhydrous salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, and is generally from about 1.5% to about 15%, preferably from about 2% to about 10%, and most preferably from about 3% to about 8%, by weight of the composition. Some or all of the tetrasodium pyrophosphate is undissolved in the product and is present as tetrasodium pyrophosphate particles. Pyrophosphate ions in different protonated states (e.g., $HP_2O_7^{-3}$) may also exist depending upon the pH of the composition and if part of the tetrasodium pyrophosphate is dissolved.

The pyrophosphate salts are described in more detail in Kirk & Othmer, *Encyclopedia of Chemical Technology*, Third Edition, Volume 17, Wiley-Interscience Publishers (1982), incorporated herein by reference in its entirety, including all references incorporated into Kirk & Othmer.

Optional anticalculus agents that may be used in combination with the pyrophosphate salt include such known materials as synthetic anionic polymers [including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propoane sulfonic acid (AMPS)], zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof.

Calcium Peroxide

The present invention also includes calcium peroxide. The following amounts represent the amount of peroxide raw material, although the calcium peroxide may contain ingredients other than the peroxide raw material. The present compositions contain from about 0.01% to about 5%, preferably from about 0.1% to about 3%, more preferably from about 0.2% to about 1%, and most preferably from about 0.3% to about 0.8% of calcium peroxide, by weight of the total composition.

pH

The pH of the present compositions is adjusted to a neat pH range of from about 9.0 to about 10.5. The term "neat pH", as used herein, is defined as the pH of the composition before the composition is diluted or contacted by the mouth. The neat pH is adjusted by the use of buffering agents. The neat pH of the present composition is from about 9.0 to about 10.5, preferably from about 9.2 to about 10.2, and more preferably from about 9.5 to about 10.

Water

Water is also contained in the present invention. Water used in the preparation of these compositions should preferably be of low ion content and free of organic impurities. The "total water content" of the composition, as used herein, includes the free water which is added plus the water which is introduced with other materials, such as with sorbitol, silica, color solutions, or surfactant solutions. The total water content of the present invention is from about 9.1% to about 20%, preferably from about 0.2% to about 14%, more preferably from about 9.5% to about 13%, and most preferably from about 10% to about 11%, by weight of the total composition.

Alkali Metal Bicarbonate Salt

The present invention may also include an alkali metal bicarbonate salt.

Alkali metal bicarbonate salts are soluble in water and unless stabilized, tend to release carbon dioxide in an aqueous system. Sodium bicarbonate, also known as baking soda, is the preferred alkali metal bicarbonate salt. The present compositions may contain from about 0.5% to about 40%, preferably from about 0.5% to about 20%, more preferably from about 0.5% to about 5%, and most preferably from about 0.8% to about 2% of an alkali metal bicarbonate salt, by weight of the total composition.

Xylitol

The present invention may also include xylitol. Xylitol is a sugar alcohol that is used as a sweetener and humectant. Xylitol may provide a therapeutic effect, such as an antibacterial or anticaries effect. The present compositions may comprise xylitol at a level from about 0.01% to about 25%, preferably from about 3% to about 15%, more preferably from about 5% to about 12%, and most preferably from about 9% to about 11%, by weight of the total composition.

Aqueous Carriers

In preparing the present compositions, it is desirable to add one or more aqueous carriers to the compositions. Aqueous carriers contain materials that are well known in the art and readily chosen by one skilled in the art based on the physical and aesthetic properties desired for the compositions being prepared. Aqueous carriers typically comprise from about 80% to about 98%, and preferably from about 85% to about 95%, by weight of the total composition.

The present invention compositions in the form of toothpastes, typically contain some thickening material or binders to provide a desirable consistency. Preferred thickening agents are carboxyvinyl polymers, carrageenan, hydroxyethyl cellulose, and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate, lithium aluminum magnesium silicate (tradename Laponite), or finely divided silica can be used as part of the thickening agent to further improve texture. Thickening agents can be used in an amount of from about 0.1% to about 15%, by weight of the total composition.

Another optional component of the compositions desired herein is a humectant. The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, and other edible polyhydric alcohols. Polyethylene glycols are one of the preferred humectants.

Polyethylene glycols useful herein are those which are liquids at room temperature or have a melting point slightly there above. Liquid and low-melting polyethylene glycols are commercially available from Union Carbide under the Carbowax® tradename. Preferred are those polyethylene glycols having a molecular weight range of from about 200 to about 2000 and corresponding n values of from about 4 to about 40. More preferred are polyethylene glycols having a molecular weight range of from about 400 to about 1600 and most preferred are polyethylene glycols having a molecular weight range of from about 570 to about 630. The humectant generally comprises from about 0% to 70%, and preferably from about 15% to 55%, by weight of the compositions herein.

Buffering agents may be used to adjust the pH of the present compositions. Buffering agents, as used herein, refer to agents that can be used to adjust the pH of the compositions to a neat pH range of from about 9.0 to about 10.5. These agents include alkali metal hydroxides, carbonates, sesquicarbonates, borates, and silicates. Specific buffering agents include monosodium phosphate, trisodium phosphate, sodium hydroxide, potassium hydroxide, and sodium carbonate. Buffering agents can be used at a level of from about 0.5% to about 10%, by weight of the present compositions.

An abrasive polishing material may also be included in the toothpaste compositions. The abrasive polishing material contemplated for use in the compositions of the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al in U.S. Pat. No. 3,070,510, issued Dec. 25, 1962, incorporated herein by reference. Mixtures of abrasives may also be used.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975, both incorporated herein by reference.

Preferred are the silica xerogels marketed under the trade name "Syloid" by the W.R. Grace & Company, Davison Chemical Division. Also preferred are the precipitated silica materials such as those marketed by the J. M. Huber Corporation under the trade name, "Zeodent", particularly the silica carrying the designation "Zeodent 119". The types of silica dental abrasives useful in the toothpastes of the present invention are described in more detail in Wason, U.S. Pat. No. 4,340,583, issued Jul. 29, 1982, incorporated herein by reference. The abrasive in the toothpaste compositions described herein is generally present at a level of from about 6% to about 70%, by weight of the composition. Preferably, toothpastes contain from about 10% to about 50% of abrasive, by weight of the composition.

The present composition may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976, incorporated herein in its entirety by reference. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene sorbitan esters (sold under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al., U.S. Pat. No. 4,051,234, issued Sep. 27, 1977, incorporated herein by reference in its entirety. The present compositions may comprise one or more surfactants each at a level of from about 0.25% to about 10%, preferably from about 0.5% to about 8%, and most preferably from about 1% to about 6%, by weight of the composition.

Titanium dioxide may also be added to the present composition. Titanium dioxide is a white powder which adds opacity to the compositions. Titanium dioxide may comprise from about 0.25% to about 5%, by weight of the compositions.

Coloring agents may also be added to the present composition. The coloring agent may be in the form of an aqueous solution, preferably a 1% color solution. Color solutions may comprise from about 0.01% to about 5%, by weight of the composition.

A flavor system can also be added to the compositions. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the paramenthan carboxyamide agents such as N-ethyl-p-menthan-3-carboxamide (known commercially as "WS-3") and mixtures thereof. A flavor system is generally used in the compositions at levels of from about 0.001% to about 5%, by weight of the composition.

Sweetening agents can be added to the compositions. These include sodium saccharin, dextrose, sucrose, lactose, maltose, levulose, aspartame, sodium cyclamate, D-tryptophan, dihydrochalcones, acesulfame, and mixtures thereof. Sweetening agents are generally used in toothpastes at levels of from about 0.005% to about 5%, by weight of the composition.

The present invention may also include other agents. Included among such agents are water insoluble non-cationic agents such as triclosan and other agents of the type disclosed in Parran, Jr. et al., U.S. Pat. No. 5,015,466, issued May 14, 1991, incorporated by reference herein in its entirety.

The composition may be a multilayer toothpaste composition. This composition may comprise two or more separate layers which are in contact with each other. Preferably, the separate layers are pastes and gels that when extruded from the tube, appear as combination paste/gel stripes. One of the layers in this paste/gel stripe combination must comprise all of the essential components, while the other layers may contain less than all of the essential components and may be any dentifrice formulation. Preferably, the gel layers do not comprise the essential component of calcium peroxide.

Alternatively, the dentifrice compositions may be physically separated in a dentifrice dispenser. The dispenser may be a tube, pump, or any other container suitable for dispensing toothpaste. Dual compartment packages suitable for this purpose are described in U.S. Pat. No. 4,528,180, issued Jul. 9, 1985; U.S. Pat. No. 4,687,663, issued Aug. 18, 1987; and U.S. Pat. No. 4,849,213, issued Jul. 18, 1989, all to Shaeffer, all incorporated herein in their entirety. The dispenser will deliver approximately equal amounts of each dentifrice composition through an opening. The compositions may intermix once dispensed. Alternatively, the oral formulation may be delivered from a kit containing two separate dispensers which are used to deliver two dentifrice compositions that are both used simultaneously.

Method of Manufacturing

Toothpaste compositions comprising a soluble fluoride source capable of providing from about 50 ppm to about 3500 ppm of free fluoride ions, an amount of at least about 1.5% tetrasodium pyrophosphate, from about 0.01% to about 5% of calcium peroxide; and from about 80% to about 98% of one or more aqueous carriers, are made by a process comprising the steps of: (a) preparing a mixture of a soluble fluoride ion source and one or more aqueous carrier materials; (b) adding tetrasodium pyrophosphate and calcium peroxide, all at once or in portions, under conditions wherein less than about 20% of the total pyrophosphate and calcium peroxide are dissolved in the dentifrice mixture; and wherein further any remaining aqueous carrier materials not added to the mixture during step (a) are added in whole or in part in step (b) or thereafter, either by themselves or with any remaining amount of the tetrasodium pyrophosphate or calcium peroxide, under conditions such that less than about 20% of the total pyrophosphate and calcium peroxide are dissolved in the mixture; and (c) heating the mixture to a temperature range of from about 38° C. (100° F.) to about 71° C. (160° F.) and preferably to a temperature range of from about 52° C. (125° F.) to about 57° C. (135° F.). The amount of pyrophosphate dissolved in the mixture for the methods and compositions of the present invention is preferably less than about 10% by weight of the total pyrophosphate present in the compositions and the amount of calcium peroxide dissolved in the mixtures is preferably less than about 10% by weight of the total amount of calcium peroxide present in the compositions.

The dentifrice mixtures will have a viscosity of from about 10 to about 60 Brookfield units at 23° C. in bulk or packed product from about 10 minutes to about two hours after being made or packed. The viscosity then builds to a viscosity of from about 30 to about 125 Brookfield units at 23° C. in bulk or packed product after about one month or more after being made or packed. Preferably, the viscosity is from about 20 to about 50 Brookfield units at 23° C. in bulk or packed product from about 10 minutes to about two hours after being made or packed and the viscosity builds to a viscosity of from about 60 to about 80 Brookfield units at 23° C. in bulk or packed product after about one month or more after being made or packed. The viscosity is measured with a Brookfield Synchrolectric Viscometer Model RVT/2 using a T-E spindle at 2.5 revolutions per minute.

Preferably, one or more of the following process conditions are controlled as follows to limit the solubility of the tetrasodium pyrophosphate and calcium peroxide in the dentifrice mixture: (1) the neat pH of the process mixture is above about pH 8, preferably above about pH 9, during and after the tetrasodium pyrophosphate and calcium peroxide additions are made to the mixture; and (2) the tetrasodium pyrophosphate salt and peroxide are two of the last components to be added to the mixture, preferably after all or much of the other sodium-containing salts present in the composition have been added to the mixture. By these methods, the dissolved tetrasodium pyrophosphate salt is less likely to recrystalize in the form of glass-like crystal particles of tetrasodium pyrophosphate decahydrate and the peroxide is less likely to breakdown and react with the fluoride to form calcium fluoride.

During step (c), the heating step, the mixture is heated to a temperature range of from about 38° C. (100° F.) to about 71° C. (160° F.) and preferably to a temperature range of from about 52° C. (125° F.) to about 57° C. (135° F.). One or more heating variables may be controlled during this step. The heating variables include: the rate of heating the mixture to the temperature range, the amount of time that the composition is kept at this temperature range, and the rate of cooling the mixture from the temperature range. Additionally, another heating variable is homogenization. Homogenization of the mixture may occur while the mixture is within the temperature range.

After step (c), the toothpaste is fed into a suitable dispensing tube or container. After filling the tube with toothpaste, the open end of the tube is sealed. If the toothpaste is to be a multilayer composition, the desired toothpaste layers are led in parallel streams to form a multilayered appearance and then the op en end of the tube is sealed. The dentifrice layers will be extruded in the desired multilayer configuration when dispensed from the tube.

Method of Treatment

The present invention compositions additionally relate to a method for reducing the incidence of calculus on dental enamel. The method of treatment herein comprises contacting the dental enamel surfaces in the mouth with the oral compositions according to the present invention.

The following examples further describe and demonstrate embodiments within the scope of the present invention. These examples are given solely for the purpose of illustration and are not to be construed as limitations of the present invention as many variations thereof are possible without departing from the spirit and scope.

EXAMPLE I

| Ingredient | Weight % |
|---|---|
| Glycerin | 28.885 |
| Polyethylene Glycol 12 | 1.000 |
| Xanthan Gum | 0.300 |
| Carboxymethylcellulose | 0.200 |
| Water | 5.000 |
| Sodium Saccharin | 0.450 |
| Sodium Fluoride | 0.243 |
| Poloxamer 407 | 2.000 |
| Sodium Alkyl Sulfate [a] | 6.000 |
| Flavor | 1.150 |
| Sodium Carbonate | 2.800 |
| Titanium Dioxide | 1.000 |
| Silica | 20.000 |
| Sodium Bicarbonate | 10.000 |
| Propylene Glycol | 10.562 |
| Tetrasodium Pyrophosphate | 8.410 |
| Calcium Peroxide | 2.000 |

Example I is prepared as follows: Add approximately half of the glycerin to a mixing vessel. Disperse the thickening agents, carboxymethyl cellulose and xanthan gum, in the propylene glycol. Add this mixture of dispersed thickening agents in propylene glycol to the mixing vessel and add the polyethylene glycol. Dissolve the is sodium fluoride and sodium saccharin in water and add to the mixture. Add the poloxamer. The flavor and sodium alkyl sulfate are then added. Next, add the sodium carbonate, titanium dioxide, and the silica. Add the sodium bicarbonate. Disperse the tetrasodium pyrophosphate in the remaining glycerin and add to the mixture. Finally, add the calcium peroxide. Stir the mixture until homogeneous and then heat the mixture to a temperature range of from about 110° F. to about 160° F. This temperature should be maintained for about 30–60 minutes. Finally, the mixture may be cooled and deaerated.

EXAMPLE II

| Ingredient | Weight % |
|---|---|
| Glycerin | 28.990 |
| Polyethylene Glycol 12 | 3.000 |
| Xanthan Gum | 0.400 |
| Carboxymethylcellulose | 0.250 |
| Water | 5.000 |
| Sodium Saccharin | 0.450 |
| Sodium Fluoride | 0.243 |
| Xylitol | 10.000 |
| Poloxamer 407 | 3.000 |
| Sodium Alkyl Sulfate [a] | 6.000 |
| Flavor | 1.150 |
| Sodium Carbonate | 2.800 |
| Titanium Dioxide | 1.000 |
| Silica | 20.000 |
| Sodium Bicarbonate | 1.000 |
| Propylene Glycol | 11.571 |
| Tetrasodium Pyrophosphate | 5.046 |
| Calcium Peroxide | 0.100 |

EXAMPLE III

| Ingredient | Weight % |
|---|---|
| Glycerin | 27.050 |
| Polyethylene Glycol 12 | 2.000 |
| Xanthan Gum | 0.300 |
| Carboxymethylcellulose | 0.200 |
| Water | 5.000 |
| Sodium Saccharin | 0.450 |
| Sodium Fluoride | 0.243 |
| Xylitol | 10.000 |
| Poloxamer 407 | 2.000 |
| Sodium Alkyl Sulfate [a] | 6.000 |
| Flavor | 1.100 |
| Sodium Carbonate | 2.600 |
| Titanium Dioxide | 1.000 |
| Silica | 20.000 |
| Sodium Bicarbonate | 1.500 |
| Propylene Glycol | 15.011 |
| Tetrasodium Pyrophosphate | 5.046 |
| Calcium Peroxide | 0.500 |

Examples II and III are prepared as follows: Add approximately half of the glycerin to a mixing vessel. Disperse the thickening agents, carboxymethyl cellulose and xanthan gum, in the propylene glycol. Add this mixture of dispersed thickening agents in propylene glycol to the mixing vessel and add the polyethylene glycol. Dissolve the sodium fluoride and sodium saccharin in water and add to the mixture. Add the xylitol and poloxamer. The flavor and sodium alkyl sulfate are then added. Next, add the sodium carbonate, titanium dioxide, and the silica. Add the sodium bicarbonate. Disperse the tetrasodium pyrophosphate in the remaining glycerin and add to the mixture. Finally, add the calcium peroxide. Stir the mixture until homogeneous and then heat the mixture to a temperature range of from about 110° F. to about 160° F. This temperature should be maintained for about 30–60 minutes. Finally, the mixture may be cooled and deaerated.

EXAMPLE IV

| Ingredient | Weight % |
|---|---|
| Glycerin | 28.611 |
| Polyethylene Glycol 6 | 1.000 |
| Xanthan Gum | 0.350 |
| Carboxymethylcellulose | 0.250 |
| Water | 6.400 |
| Sodium Saccharin | 0.300 |
| Sodium Fluoride | 0.243 |
| Sodium Alkyl Sulfate [a] | 6.000 |
| Flavor | 0.900 |
| Sodium Carbonate | 2.800 |
| Titanium Dioxide | 0.500 |
| Silica | 10.000 |
| Sodium Bicarbonate | 30.000 |
| Propylene Glycol | 7.500 |
| Tetrasodium Pyrophosphate | 5.046 |
| Calcium Peroxide | 0.100 |

Example IV is prepared as follows: Add approximately half of the glycerin to a mixing vessel. Disperse the thickening agents, carboxymethyl cellulose and xanthan gum, in the propylene glycol. Add this mixture of dispersed thickening agents in propylene glycol to the mixing vessel and add the polyethylene glycol. Dissolve the sodium fluoride and sodium saccharin in water and add to the mixture. The flavor and sodium alkyl sulfate are then added. Next, add the sodium carbonate, titanium dioxide, and the silica. Add the sodium bicarbonate. Disperse the tetrasodium pyrophosphate in the remaining glycerin and add to the mixture.

Finally, add the calcium peroxide. Stir the mixture until homogeneous and then heat the mixture to a temperature range of from about 110° F. to about 160° F. This temperature should be maintained for about 30–60 minutes. Finally, the mixture may be cooled and deaerated.

EXAMPLE V

| Ingredient | Weight % |
| --- | --- |
| Glycerin | 24.461 |
| Polyethylene Glycol 12 | 1.000 |
| Xanthan Gum | 0.500 |
| Carboxymethylcellulose | 0.350 |
| Water | 11.500 |
| Sodium Saccharin | 0.450 |
| Sodium Fluoride | 0.243 |
| Xylitol | 20.000 |
| Sodium Alkyl Sulfate (a) | 6.000 |
| Flavor | 1.150 |
| Sodium Carbonate | 2.800 |
| Titanium Dioxide | 1.000 |
| Silica | 15.000 |
| Propylene Glycol | 10.000 |
| Tetrasodium Pyrophosphate | 5.046 |
| Calcium Peroxide | 0.500 |

(a) 27.9% solution of sodium alkyl sulfate in water

Example V is prepared as follows: Add approximately half of the glycerin to a mixing vessel. Disperse the thickening agents, carboxymethyl cellulose and xanthan gum, in the propylene glycol. Add this mixture of dispersed thickening agents in propylene glycol to the mixing vessel and add the polyethylene glycol. Dissolve the sodium fluoride and sodium saccharin in water and add to the mixture. Add the xylitol. The flavor and sodium alkyl sulfate are then added. Next add the sodium carbonate, titanium dioxide, and the silica. Disperse the tetrasodium pyrophosphate in the remaining glycerin and add to the mixture. Finally, add the calcium peroxide. Stir the mixture until homogeneous and then heat the mixture to a temperature range of from about 110° F. to about 160° F. This temperature should be maintained for about 30–60 minutes. Finally, the mixture may be cooled and deaerated.

What is claimed is:

1. An oral composition comprising:
   a. a soluble fluoride source capable of providing from about 50 ppm to about 3500 ppm of free fluoride ions;
   b. an amount of at least about 1.5% tetrasodium pyrophosphate;
   c. from about 0.01% to about 5% of calcium peroxide;
   d. from about 80% to about 98% of one or more aqueous carriers;
   wherein the oral composition has a neat pH of from about 9.0 to about 10.5 and a total water content of from 9.1% to about 20%.

2. The oral composition according to claim 1 wherein the soluble fluoride source is sodium fluoride.

3. The oral composition according to claim 2 wherein the composition comprises from about 1.5% to about 15% tetrasodium pyrophosphate of which some or all of the tetrasodium pyrophosphate is undissolved in the product and is present as tetrasodium pyrophosphate particles.

4. The oral composition according to claim 3 wherein the calcium peroxide is in an amount of from about 0.1% to about 3.0%.

5. The oral composition according to claim 4 wherein the neat pH is from about 9.2 to about 10.2.

6. The oral composition according to claim 5 where the total water content is from about 9.2% to about 14%.

7. The oral composition according to claim 6 wherein the aqueous carriers contain materials selected from the group consisting of thickening materials, humectants, water, buffering agents, abrasive polishing materials, surfactants, titanium dioxide, flavor system, sweetening agents, coloring agents, and mixtures thereof.

8. The oral composition according to claim 7 wherein the composition is a multilayer composition which is extruded from a tube in combination paste/gel stripes.

9. An oral composition comprising:
   a. a soluble fluoride source capable of providing from about 50 ppm to about 3500 ppm of free fluoride ions;
   b. an amount of at least about 1.5% tetrasodium pyrophosphate;
   c. from about 0.01% to about 5.0% of calcium peroxide;
   d. from about 0.5% to about 40% of an alkali metal bicarbonate salt; and
   e. from about 80% to about 98% of one or more aqueous carriers;
   wherein the oral composition has a neat pH of from about 9.0 to about 10.5 and a total water content of from about 9.1% to about 20%.

10. The oral composition according to claim 9 wherein the soluble fluoride source is sodium fluoride.

11. The oral composition according to claim 10 wherein the composition comprises from about 1.5% to about 15% tetrasodium pyrophosphate of which some or all of the tetrasodium pyrophosphate is undissolved in the product and is present as tetrasodium pyrophosphate particles.

12. The oral composition according to claim 11 wherein the calcium peroxide is in an amount of from about 0.1% to about 3.0%.

13. The oral composition according to claim 12 wherein the neat pH is from about 9.2 to about 10.2.

14. The oral composition according to claim 13 where the total water content is from about 0.2% to about 14%.

15. The oral composition according to claim 14 further comprising from about 0.01% to about 25% of xylitol.

16. The oral composition according to claim 15 wherein the aqueous carriers contain materials selected from the group consisting of thickening materials, humectants, water, buffering agents, abrasive polishing materials, surfactants, titanium dioxide, flavor system, sweetening agents, coloring agents, and mixtures thereof.

17. The oral composition according to claim 16 wherein the composition is a multilayer composition which is extruded from a tube in combination paste/gel stripes.

18. A method for reducing the incidence of calculus on dental enamel comprising contacting the enamel surfaces in the mouth with the oral composition according to claim 2.

19. A method for reducing the incidence of calculus on dental enamel comprising contacting the enamel surfaces in the mouth with the oral composition according to claim 10.

20. The oral composition comprising a soluble fluoride source capable of providing from about 50 ppm to about 3500 ppm of free fluoride ions; an amount of at least about 1.5% tetrasodium pyrophosphate; from about 0.01% to about 5% of calcium peroxide; and from about 80% to about 98% of one or more aqueous carriers;
   wherein the oral composition has a neat pH of from about 9.0 to about 10.5 and a total water content of from about 9.1% to 20%, produced according to a process comprising the steps of:
   a. preparing a mixture of a soluble fluoride source and one or more aqueous carrier materials;
   b. adding tetrasodium pyrophosphate and calcium peroxide, all at once or in portions, under conditions wherein less than about 20% of the total pyrophosphate and calcium peroxide are dissolved in the mixture, and wherein any further remaining aqueous carrier materials is not added to the mixtures during step (a) are added in whole or in part in step (b) or thereafter, either by themselves or with any remaining amount of the tetrasodium pyrophosphate or calcium peroxide under conditions such that less than about 20% of the total pyrophosphate and calcium peroxide are dissolved in the mixture; and c. heating the mixture to a temperature range of from about 38° C. to about 71° C.

* * * * *

UNITED STATES PATENT AND TRADEMARK OFFICE
CERTIFICATE OF CORRECTION

PATENT NO. : 5,820,852
DATED : October 13, 1998
INVENTOR(S) : STEVEN CARL BURGESS, CONNIE LYNN SHEETS It is certified that error appears in the above-identified patent and that said Letters Patent is hereby corrected as shown below:

Column 4, line 10, "0.2%" should be --9.2%--.
Column 9, line 33, the word "is" should be deleted
Column 12, line 36, "0.2%" should be --9.2%--.

Signed and Sealed this

Sixteenth Day of March, 1999

Attest:

Attesting Officer

Q. TODD DICKINSON

Acting Commissioner of Patents and Trademarks